United States Patent
Hafner et al.

(10) Patent No.: US 9,084,586 B2
(45) Date of Patent: Jul. 21, 2015

(54) SURGICAL DRIVE UNIT, SURGICAL INSTRUMENT AND SURGICAL DRIVE SYSTEM

(75) Inventors: Ronald Hafner, Leibertingen (DE); Ernst Moosmann, Leibertingen-Altheim (DE); Juergen Schneider, Tuttlingen (DE); Birgit Schnell, Neuhausen (DE)

(73) Assignee: Aesculap AG, Tuttlingen (DE)

( * ) Notice: Subject to any disclaimer, the term of this patent is extended or adjusted under 35 U.S.C. 154(b) by 652 days.

(21) Appl. No.: 12/925,692

(22) Filed: Oct. 26, 2010

(65) Prior Publication Data

US 2011/0208170 A1    Aug. 25, 2011

Related U.S. Application Data

(63) Continuation of application No. PCT/EP2009/055239, filed on Apr. 29, 2009.

(30) Foreign Application Priority Data

May 14, 2008  (DE) .......................... 10 2008 024 438

(51) Int. Cl.
*A61B 17/00* (2006.01)
*A61B 17/32* (2006.01)
*G06F 19/00* (2011.01)
*A61C 1/02* (2006.01)
*A61B 19/00* (2006.01)

(52) U.S. Cl.
CPC ................. *A61B 17/00* (2013.01); *A61B 19/44* (2013.01); *A61B 2017/00017* (2013.01); *A61B 2017/00084* (2013.01); *A61B 2017/00199* (2013.01); *A61B 2017/00398* (2013.01); *A61B 2017/00464* (2013.01); *A61B 2017/00482* (2013.01); *A61B 2019/448* (2013.01)

(58) Field of Classification Search
CPC ... A61B 19/22; A61B 19/44; A61B 2019/448
USPC .................................. 606/1; 700/245; 901/30
See application file for complete search history.

(56) References Cited

U.S. PATENT DOCUMENTS 4,194,178 A * 3/1980 Dumbeck ................ 340/870.17
5,814,900 A * 9/1998 Esser et al. .................... 307/104
(Continued)

FOREIGN PATENT DOCUMENTS

DE      102 25 232     12/2002
DE      102 25 857      1/2004
(Continued)

*Primary Examiner* — Aaron Roane
(74) *Attorney, Agent, or Firm* — Lipsitz & McAllister, LLC

(57) ABSTRACT

In order to so improve a surgical drive unit of a surgical instrument, comprising a motor with at least two motor windings, and a memory device for storing data characterizing the drive unit and/or the motor, that the reliability of drive units, instruments and drive systems of the kind described at the outset is enhanced, it is proposed that the drive unit comprise a first transmitting and receiving device, which is connected to the memory device, and a second transmitting and receiving device, which is connected to at least two connection contacts of the motor, and that the first and second transmitting and receiving devices be configured and interact in such a way that data are transferable between them in a contactless manner.

An improved surgical instrument and a further developed surgical drive system are also proposed.

24 Claims, 5 Drawing Sheets

(56) References Cited

U.S. PATENT DOCUMENTS

| | | |
|---|---|---|
| 7,258,546 B2 | 8/2007 | Beier et al. |
| 2003/0093103 A1 | 5/2003 | Malackowski et al. |
| 2004/0004460 A1* | 1/2004 | Fitch et al. .................... 320/108 |
| 2004/0133189 A1 | 7/2004 | Sakurai |
| 2004/0209223 A1 | 10/2004 | Beier et al. |
| 2004/0220602 A1 | 11/2004 | Deng et al. |
| 2004/0225310 A1* | 11/2004 | Culp et al. .................... 606/170 |
| 2006/0240382 A1* | 10/2006 | Voillat ............................ 433/99 |
| 2008/0077170 A1 | 3/2008 | Kluge et al. |
| 2008/0262654 A1* | 10/2008 | Omori et al. .................. 700/245 |

FOREIGN PATENT DOCUMENTS

| | | |
|---|---|---|
| EP | 0 788 778 | 8/1997 |
| EP | 1 872 823 | 1/2008 |
| EP | 2 042 120 | 4/2009 |
| JP | 2004208922 | 7/2004 |
| WO | 98/06338 | 2/1998 |

* cited by examiner

US 9,084,586 B2

SURGICAL DRIVE UNIT, SURGICAL INSTRUMENT AND SURGICAL DRIVE SYSTEM

CROSS-REFERENCE TO RELATED APPLICATIONS

This application is a continuation of international application number PCT/EP2009/055239 filed on Apr. 29, 2009 and claims the benefit of German application number 10 2008 024 438.4 filed on May 14, 2008.

The present disclosure relates to the subject matter disclosed in international application number PCT/EP2009/055239 of Apr. 29, 2009 and German application number 10 2008 024 438.4 of May 14, 2008, which are incorporated herein by reference in their entirety and for all purposes.

FIELD OF THE INVENTION

The present invention relates to surgical drive units generally, and more specifically to a surgical drive unit of a surgical instrument, comprising a motor with at least two motor windings, and a memory device for storing data characterizing the drive unit and/or the motor.

The present invention also relates to surgical instruments generally, and more specifically, to a surgical instrument comprising a drive unit and a surgical tool connected or connectable to the drive unit and drivable by the drive unit, the drive unit comprising a motor with at least two motor windings, and a memory device for storing data characterizing the drive unit and/or the motor.

The present invention further relates to surgical drive systems generally, and more specifically to a surgical drive system comprising at least one control device and at least two surgical drive units connectable to and controllable by the control device, or surgical instruments comprising surgical drive units, at least one of the at least two surgical drive units comprising a motor with at least two motor windings, and a memory device for storing data characterizing the drive unit and/or the motor.

BACKGROUND OF THE INVENTION

Devices of the kind described at the outset are known from DE 102 25 857 A1, for example. The drive units or motors of the drive system described therein are each equipped with a memory device in which data characterizing the type of motor are stored. These data are stored in the memory device at the manufacturing stage and cannot be altered by the user. In motors with three motor windings, three connection lines are required for connecting the motor to a motor controller for controlling the motor. Further control and/or data lines are required for transferring data characterizing the respective motor to the controller. Consequently, depending on the requirements, a corresponding number of contacts has to be provided for the connection lines of the motor and the control and/or data lines. However, as the drive units have to be cleaned and possibly steam-sterilized after a surgical procedure, contact problems cannot be excluded, in particular, with the control and data lines, which are not connected to the motor windings.

It is, therefore, desirable to improve the reliability of drive units, instruments and drive systems of the kind described at the outset.

SUMMARY OF THE INVENTION

In a first aspect of the invention, a surgical drive unit of a surgical instrument comprises a motor with at least two motor windings; and a memory device for storing data characterizing at least one of the drive unit and the motor. The drive unit comprises a first transmitting and receiving device, which is connected to the memory device, and a second transmitting and receiving device, which is connected to at least two connection contacts of the motor. The first and second transmitting and receiving devices are configured and interact in such a way that data are transferable between them in a contactless manner.

In a second aspect of the invention, a surgical drive unit of a surgical instrument comprises a motor with at least two motor windings; and a memory device for storing data characterizing at least one of the drive unit and the motor. The drive unit comprises a motor disabling device for disabling operation of the motor.

In a third aspect of the invention, a surgical instrument comprises a drive unit and a surgical tool connected or connectable to the drive unit and drivable by the drive unit. The drive unit comprises a motor with at least two motor windings, and a memory device for storing data characterizing at least one of the drive unit and the motor. The drive unit comprises a first transmitting and receiving device, which is connected to the memory device, and a second transmitting and receiving device, which is connected to at least two connection contacts of the motor. The first and second transmitting and receiving devices are configured and interact in such a way that data are transferable between them in a contactless manner.

In a fourth aspect of the invention, a surgical drive system comprise at least one control device; and at least two surgical drive units connectable to and controllable by said control device, or surgical instruments comprising surgical drive units. At least one of the at least two surgical drive units comprise a motor with at least two motor windings, and a memory device for storing data characterizing at least one of the drive unit and the motor. The drive unit comprises a first transmitting and receiving device, which is connected to the memory device, and a second transmitting and receiving device, which is connected to at least two connection contacts of the motor. The first and second transmitting and receiving devices are configured and interact in such a way that data are transferable between them in a contactless manner.

BRIEF DESCRIPTION OF THE DRAWING FIGURES

The foregoing summary and the following description may be better understood in conjunction with the drawing figures, of which:

DETAILED DESCRIPTION OF PREFERRED EMBODIMENTS OF THE INVENTION

Figure 1:
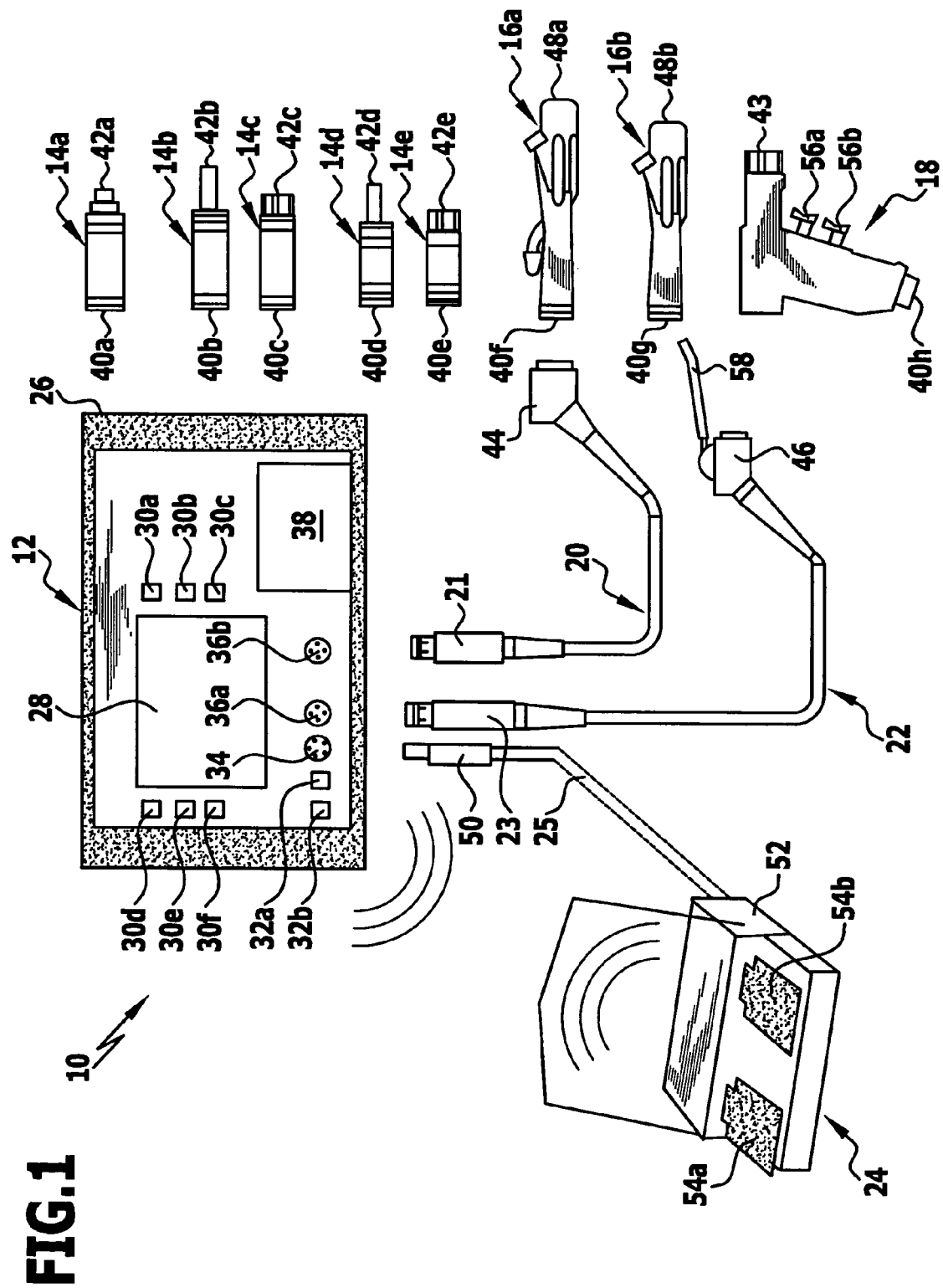
FIG. 1 is a diagrammatic overview representation of a surgical drive system.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical drive unit of a surgical instrument comprises a motor with at least two-motor windings; and a memory device for storing data characterizing at least one of the drive unit and the motor. The drive unit comprises a first transmitting and receiving device, which is connected to the memory device, and a second transmitting and receiving device, which is connected to at least two connection contacts of the motor. The first and second transmitting and receiving devices are configured and interact in such a way that data are transferable between them in a contactless manner.

The present invention further relates to a surgical drive unit of a surgical instrument comprises a motor with at least two motor windings; and a memory device for storing data characterizing at least one of the drive unit and the motor. The drive unit comprises a motor disabling device for disabling operation of the motor.

The present invention further relates to a surgical instrument comprises a drive unit and a surgical tool connected or connectable to the drive unit and drivable by the drive unit. The drive unit comprises a motor with at least two motor windings, and a memory device for storing data characterizing at least one of the drive unit and the motor. The drive unit comprises a first transmitting and receiving device, which is connected to the memory device, and a second transmitting and receiving device, which is connected to at least two connection contacts of the motor. The first and second transmitting and receiving devices are configured and interact in such a way that data are transferable between them in a contactless manner.

The present invention further relates to a surgical drive system comprise at least one control device; and at least two surgical drive units connectable to and controllable by said control device, or surgical instruments comprising surgical drive units. At least one of the at least two surgical drive units comprise a motor with at least two motor windings, and a memory device for storing data characterizing at least one of the drive unit and the motor. The drive unit comprises a first transmitting and receiving device, which is connected to the memory device, and a second transmitting and receiving device, which is connected to at least two connection contacts of the motor. The first and second transmitting and receiving devices are configured and interact in such a way that data are transferable between them in a contactless manner.

The further development, in accordance with the invention, of known surgical drive units, which, in particular, may be parts of a surgical instrument and a surgical drive system, has, in particular, the advantage that data can be read from the memory device via the connection contacts which are conductively connected to the at least two motor windings and possibly to connection lines of the motor. Additional control or data lines are not required for reading from the memory device. In particular, in new motor generations, which together with suitable control devices enable speed detection without sensors on the motor or the drive unit and in which there is, therefore, no need to provide any data or control lines, the proposed further development in accordance with the invention is particularly well suited for totally dispensing with the data or control lines. For example, the inquiry as to the type of motor can then take place, prior to starting operation of the motor, via the motor connection contacts or lines which are connected to the first transmitting and receiving device, by data relating to the type of motor being read from the memory device and, for example, transferred to a motor controller, in a contactless manner, by data exchange with the second transmitting and receiving device, in order to automatically set in a desired manner certain operational parameters in the motor controller. It is thus possible to prevent the motor from, for example, being supplied with excessive currents and being operated outside an admissible speed range. In any case, the possibility of dispensing with control or data lines, in accordance with the invention, reduces the number of contacts on the drive unit, which as a result of corrosion caused by cleaning and sterilization can put at risk long-term operational reliability of the drive unit.

A particularly simple and safe data exchange is possible when the first and/or the second transmitting and receiving device is/are configured as an antenna.

A particularly simple construction of the drive unit is achievable by one of the at least two motor windings forming the second transmitting and receiving device. The selected motor winding is thus accorded a double function. Firstly, it is a component of the motor as actual drive element and, secondly, it forms part of a transfer device for transferring data from the memory device, for example, to a control device in the form of a motor controller. This construction makes it possible to use the connection contacts or lines to the motor also as control or data lines, in particular, when the motor is not in operation. A connection of the control device to the second transmitting and receiving device can thus be effected directly via the motor connection contacts, i.e., via the connection contacts of the selected motor winding.

For example, data for characterizing the motor, for example, the type of motor, can be transferred in a simple way from the drive unit to a control device when data stored in the memory device are transferable in a contactless manner between the first and second transmitting and receiving devices.

A signal or data exchange between the first and second transmitting and receiving devices is particularly simple when these are configured for transmitting and receiving electromagnetic waves. Here frequencies in ranges between 30 and 500 kHz, 3 to 30 MHz, in the 433 MHz band, between 850 and 950 MHz and microwave frequencies in a range of 2.4 to 2.5 GHz are possible as frequencies.

In principle, it is conceivable to electrically conductively connect the first and second transmitting and receiving devices to each other. In particular, in order to be able to also use the second transmitting and receiving device for other purposes, it is advantageous for the first and second transmitting and receiving devices to be coupled in a contactless manner to each other. Thus, in particular, in the case of different current supply to the second transmitting and receiving device, the occurrence of damage to the drive unit can be prevented.

A particularly simple form of coupling between the first and second transmitting and receiving devices is an inductive coupling. In principle, it is also possible to capacitively couple the transmitting and receiving devices to each other.

Expediently, the surgical drive unit is equipped with a motor identification device for identifying the kind or type of surgical drive unit and/or of motor. With the motor identification device it is, for example, possible to retrieve data stored in the memory device of the drive unit relating to the kind or type of drive unit and/or motor prior to their operation and, for example, to transfer these to a control device.

The construction of the motor identification device and the drive unit is particularly simple when the motor identification device comprises the memory device. A drive unit can thus be constructed with a minimum number of components.

The construction of the surgical drive unit can be even more compact and simple when the motor identification device comprises the first transmitting and receiving device. By installing a single component, so to speak, not only the memory device but optionally also the first transmitting and receiving device can thus be installed in one assembly step in the drive unit.

Manufacture of the surgical drive unit is particularly simple and cost-effective when the motor identification device is configured as an RFID (radio-frequency identification) component. Such components, which are also referred to as RFID chips or transponder chips, are available in different designs and sizes and are suitable for installation as an assembly for performing several sub-functions. In particular, an RFID chip can comprise a transmitting and receiving device and a memory device.

In order to obtain a particularly good coupling for good exchange of signals and data, it is advantageous for the motor identification device to be disposed in close spatial proximity to the second transmitting and receiving device. Preferably, the arrangement of the first transmitting and receiving device comprised by the motor identification device is constructionally so selected that the first and second transmitting and receiving devices can interact and work together in an optimized manner.

In order that no additional energy source will be required for the motor identification device, it is expedient for it to be configured as a passive motor identification device. Of course, an active motor identification device could also be provided, which requires a supply of energy for operating its subunits. Passive motor identification devices have the advantage that they can take energy required for their operation from an electromagnetic high-frequency alternating field, which is generated by the second transmitting and receiving device.

Expediently, electromagnetic high-frequency fields of short range are generatable with the first and/or second transmitting and receiving devices. Thus, in particular, short distances between the transmitting and receiving devices can be bridged without difficulty and with high precision.

Advantageously, the memory device comprises a non-volatile memory. It is thus ensured that the data contained in the memory will be permanently maintained.

To prevent data contained in the memory device from being accidentally deleted or overwritten by a user, it is advantageous for the memory device to comprise a non-writable memory. Any tampering with the memory device in order to alter the data stored therein by the manufacturer is thereby excluded.

It is expedient for the memory device to be configured as a read-only memory (ROM). Such a memory can, for example, be written on only once, but can be read out as often as required. For example, a manufacturer can allocate to each drive unit individual data for characterizing it, for example, the type of motor, a serial number, or also a type or serial number of the drive unit as a whole.

Preferably, the motor comprises three motor windings. This makes it possible to use conventional motors to form the drive unit.

In accordance with a preferred embodiment of the invention, it may, furthermore, be provided that the drive unit comprises a motor disabling device for disabling operation of the motor. This further development is possible, in particular, also in a surgical drive unit of the kind described at the outset. With the motor disabling device it is possible to specifically define whether and when a motor of the drive unit can be operated at all, in particular, supplied with current. Only by corresponding activation or deactivation of the motor disabling device can, for example, the motor be enabled and operated.

The construction of the motor disabling device is particularly simple when it comprises a switch element which is connected to two motor connection contacts. Prior to the actual operation of the motor, it is then possible, for example, via two motor connection contacts, i.e., via two winding contacts, for example, to inquire whether the switch element is open or closed. Depending on the switch position of the switch element, it is then, for example, possible to detect in a control device whether the motor disabling device is assuming a disabling or enabling position in which motor operation is disabled or enabled.

In order to facilitate the inquiring of the motor disabling device, in particular, as to whether it is assuming a disabling or enabling position, it is expedient for the motor disabling device to comprise a frequency-dependent resistor connected in series with the switch element between two motor connection contacts. For example, in an inquiry operation of the control device, it is thus possible to conduct a high-frequency current across the two motor connection contacts. If the switch element is closed, then depending on the type of frequency-dependent resistor, the high-frequency current can either be passed through or not.

The construction of the motor disabling device is particularly simple when the frequency-dependent resistor is a capacitor. This conducts a high-frequency current and so a current flow across the two motor connection contacts can be detected when the switch element is closed.

Preferably, the surgical drive unit comprises a temperature sensor. This allows a temperature of the drive unit to be determined. For example, this may be a temperature of the drive unit before or after it is put into operation. It is also conceivable to determine a temperature during operation in order to thus create an operating temperature profile.

The construction of the drive unit is particularly simple when the motor identification device comprises the temperature sensor.

In order to be able to read temperature data from the drive unit, it is expedient for temperature data detected with the temperature sensor to be exchangeable in a contactless manner between the first and second transmitting and receiving devices. For example, the first transmitting and receiving device can be connected to the temperature sensor directly or indirectly via a corresponding circuit.

In order to be able to record after operation of the drive unit, for example, a temperature profile during operation of the drive unit, it is advantageous for the temperature sensor to comprise a temperature data memory.

In a surgical instrument further developed in accordance with the invention, it is expedient for at least one of the at least two surgical drive units to be one of the surgical drive units described above. The instrument will then have the advantages described in conjunction with the advantageous embodiments of the drive unit.

Furthermore, in a drive system further developed in accordance with the invention, it is expedient for at least one of the at least two surgical drive units to be one of the surgical drive units described above. Consequently, the surgical drive system will also have the advantages explained in conjunction with the above-described advantageous embodiments of surgical drive units.

Expediently, the at least two surgical drive units in a surgical drive system comprise different types of motor. They can then be readily identified in the manner described in detail above, in particular, automatically.

The construction of the drive system is particularly easy for a user to handle when the control device is configured as a motor controller. In particular, this may comprise corresponding interfaces for connection to connection lines or connection cables, which are connectable or connected at their other end to a drive unit or a motor of the drive system, in particular, to the motor windings. In particular, the motor controller can also comprise a display device on which prescribed and current operational data and parameters of the system can be displayed.

To enable the at least two drive units to be connected to the control device, it is advantageous for connection cables, i.e., at least one connection cable, to be provided, with which the drive units are connectable to the control device. The connection cables can be permanently connected to the drive unit or a motor or releasably connectable to these.

Advantageously, the connection cables each only comprise as many lines as motor windings comprised by the motor which is connected or connectable to them. The construction of the connection cables is thus particularly simple as no control and/or data lines need be provided. Optionally, additional control and/or data lines may, of course, be provided.

Preferably, the control device of the drive system is so configured that it is possible, in a first inquiry mode, to detect whether a drive unit is connected to the control device. Thus, before the actual operation of the drive unit is started, for example, by supplying the motor windings with current, it is possible to detect in the first inquiry mode whether a drive unit is connected at all to the control device. Here it is possible in a standby mode, so to speak, to permanently inquire whether a motor is contacted.

Furthermore, it may be advantageous for the control device to be so configured that when a drive unit is connected to the control device, it is possible, in a second inquiry mode, using the first and second transmitting and receiving devices, to read and transfer to the control device the data stored in the memory device. If the controller determines from the inquiry of the drive unit that a drive unit is contacted, then in the second inquiry mode the type of motor, for example, is inquired and transferred to the control device.

Furthermore, it may be expedient for the control device to be so configured that when a drive unit is connected to the control device, it is possible, in a third inquiry mode, by conducting a high-frequency current across the connection contacts connected to the motor disabling device, to detect whether the switch element is open or closed. In this way, it can be determined whether the motor disabling device is assuming an enabling position in which the motor can be operated, or a disabling position in which the motor cannot be operated. In dependence upon the result of the inquiry, the control device can specifically allow or not allow the motor windings to be supplied with current.

In order to avoid malfunctions of the drive system, it is advantageous for the control device to be so configured that the motor can only be supplied with current if it has been detected in the third inquiry mode that the switch element is closed. If, for example, the switch element is so configured that an operator can detect from a position of the switch element or an operating element thereof whether the motor disabling device is assuming the disabling position or the enabling position, safe operation of the drive system and its drive units can thereby be ensured.

To enable data to be read in a simple way from the memory device of the drive unit, it is advantageous for the control device to be so configured that the data stored in the memory device of the drive unit are readable and transferable to the control device using the first and second transmitting and receiving devices.

Furthermore, it may be expedient for the control device to be so configured that temperature data determined with the temperature sensor are readable and transferable to the control device using the first and second transmitting and receiving devices. In this way, it is possible to read and transfer temperature data to the control device for further processing. In particular, it is thus possible, after operation of the drive unit, to determine whether overheating of the motor occurred during the last operating period. If necessary, further supply of current to the drive unit can then be stopped in order to avoid malfunctions and, possibly, destruction of the drive unit.

Advantageously, the control device is so configured that the temperature data are only transferable in the second inquiry mode. This means that they are preferably only transferable when the drive unit is connected to the control device, but is not in operation, i.e., its motor windings are not supplied with current.

To increase the operational reliability of the drive system, it may be expedient for the control device to be so configured that operational parameters for operating a drive unit connected to the control device are automatically settable in dependence upon the data read from the memory device. In other words, this means that, for example, a maximum current and hence a maximum speed of the drive unit can be automatically limited in dependence upon the motor connected to the control device. The operational parameters to be allocated to the type of motor can, for example, be stored in a memory of the control device. It is thus also subsequently possible, without having to alter the drive units, to update operational parameters for certain motors, for example, with new program versions of a control software of the control device.

The following description of preferred embodiments of the invention serves in conjunction with the drawings for further explanation.

FIG. 1 shows diagrammatically a surgical drive system generally designated by reference numeral 10, comprising a control device in the form of a controller 12, five drive units 14a to 14e, two shaver handpieces 16a and 16b also forming drive units, a pistol handpiece 18 forming a further drive unit, two connection cables 20 and 22 and a foot control 24.

The controller 12 comprises a flat screen 28 in the form of a touch screen arranged in a housing 26. Arranged on either side of the screen 28 are three operating elements 30a to 30c and 30d to 30f, respectively.

Two switches 32a and 32b are arranged below the screen 28 on a line with a connection socket 34 for connection of the foot control 24 via an optional connection cable 25, and with two connection sockets 36a and 36b for connection of the connection cables 20 and 22, with which the drive units can be connected to the controller 12. Optionally, a connection 38 may also be provided for a fluid system for supplying fluids to and discharging fluids from a surgical site, for example, also for supplying flushing or suction channels on handpieces or tools, not shown, which are connectable to the drive units 14, the shaver handpieces 16 or the pistol handpiece 18 and together with which the drive units form surgical instruments of the drive system 10.

The drive units 14a to 14e each comprise a cable coupling 40a to 40e. These are optionally connectable to a coupling piece 44 of the connection cable 20 or a coupling piece 46 of the connection cable 22. Similarly, the two shaver handpieces 16a and 16b and the pistol handpiece 18 each comprise a cable coupling 40f, 40g and 40h, respectively, which are connectable to one of the two coupling pieces 44 or 46.

At their respective other end, the drive units 14a to 14e are equipped with handpiece or tool couplings 42a to 42e, to which handpieces, not shown, for example, drill handpieces, saw handpieces or the like can be coupled, which can be driven by the drive units 14a to 14e. Depending on their configuration, the drive units 14a to 14e can also be directly equipped with tools, not shown, such as, for example, drills or saw blades, for the formation of surgical instruments.

The drive units are preferably of sensorless configuration, i.e., they have no sensors for determining a speed of the drive unit during operation. The drive units of the drive system 10 differ not only, as shown diagrammatically in FIG. 1, externally, but also with respect to their internal construction. This means that the motors installed in the drive units may be of different types and differ, for example, in their characteristics such as, for example, minimum speed, maximum speed, maximum current and maximum torque. In addition, as in the two shaver handpieces 16a and 16b, gears may be integrated. Optionally, these may also be integrated into handpieces which can be coupled to the drive units 14 and to the pistol handpiece 18. Depending on their configuration, the handpieces themselves may also be additionally equipped with different instrument tips in the form of surgical tools.

Furthermore, the shaver handpieces 16a and 16b each, comprise a shaver coupling 48a and 48b, respectively, for connection of a shaver, for example, for use in arthroscopy.

For connection to the controller; the connection cables 20 and 22 are provided with couplings 21 and 23, via which they are connectable to the connection sockets 36a and 36b.

The foot control 24 is connected to the controller 12 via a wireless data transmission device, for example, via an infrared or radio transmission system. Optionally, a connection of the foot control 24 via a coupling piece 50 of the connection cable 25 that is connectable to the connection socket 34 is also possible. Arranged on a housing 52 of the foot control 24 are two foot-operated switches 54a and 54b, via which, in particular, an anticlockwise and a clockwise rotation of the drive units can be controlled.

The pistol handpiece 18 is equipped with two encoders 56. For example, the encoder 56a may be provided for activating clockwise rotation of the motor, the encoder 56b for activating anticlockwise rotation of the motor.

The connection cables 20 and 22 differ in that there is provided on the connection cable 22, differently from the connection cable 20, an actuating lever 58, with which an operator can activate motor operation of a drive unit 14, a shaver handpiece 16 or the pistol handpiece 18.

Figure 2:
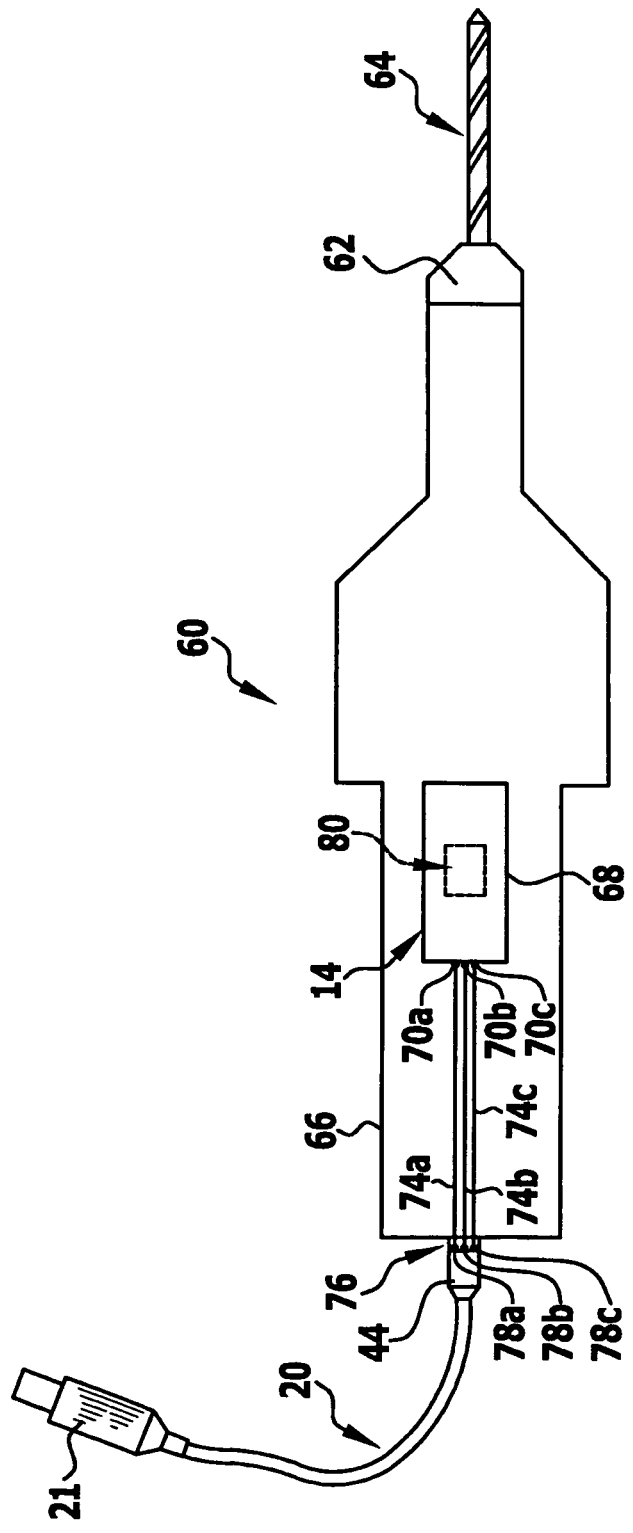
FIG. 2 is a diagrammatic representation of a surgical instrument and a control device of a surgical drive system.
Figure 3:
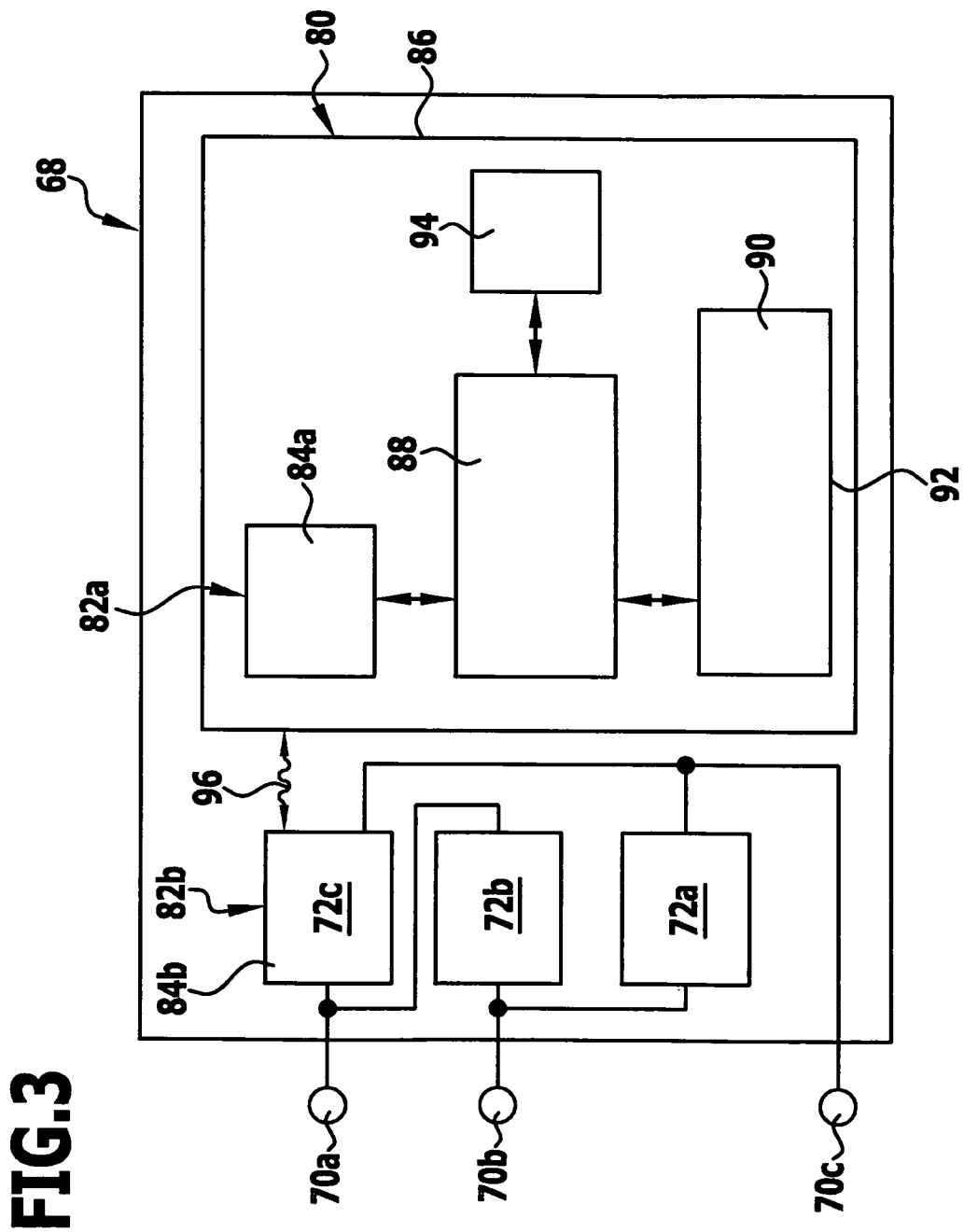
FIG. 3 is a diagrammatic representation of a motor of a drive unit with a motor identification device.
Figure 4:
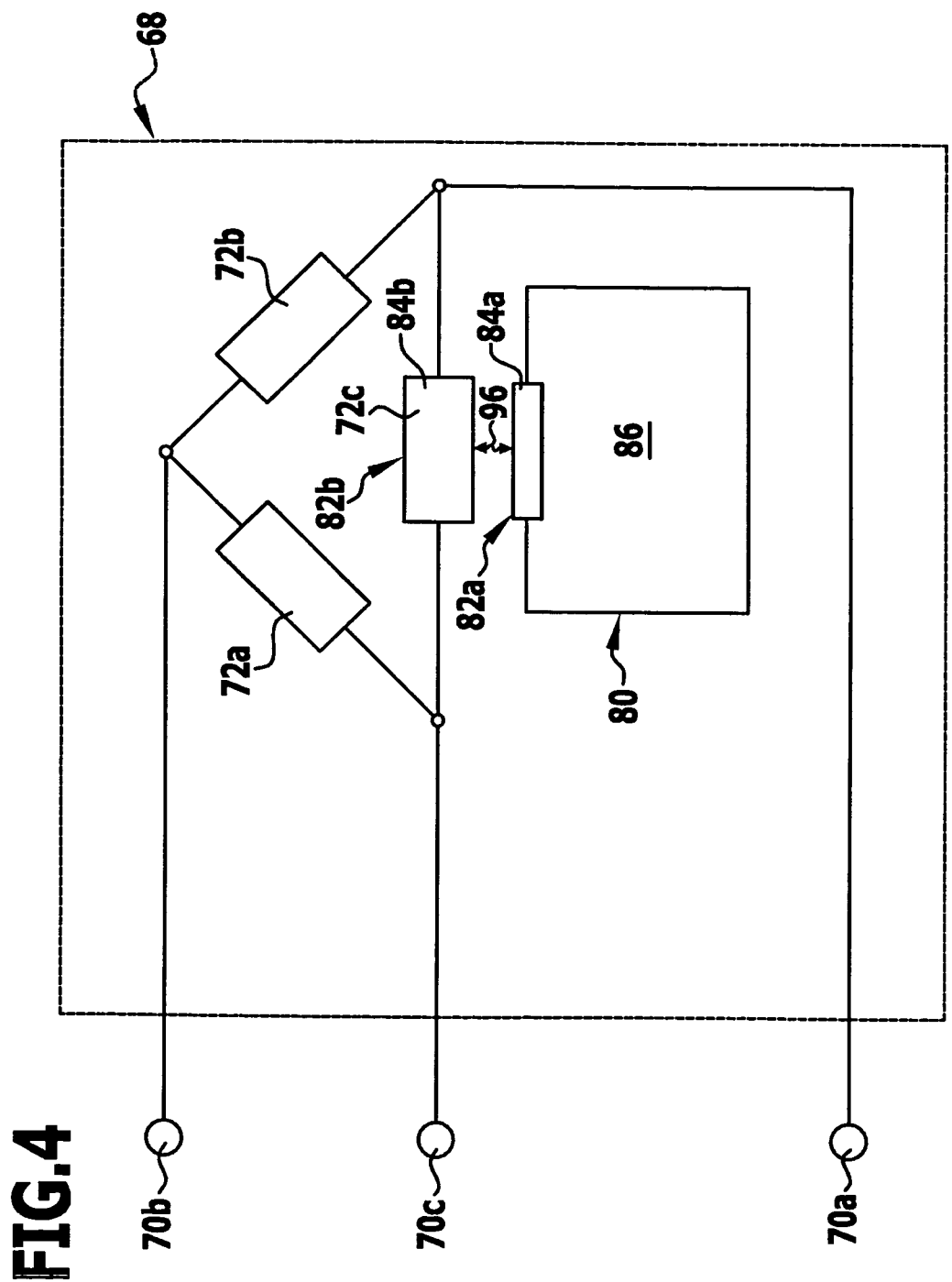
FIG. 4 is a circuit diagram of a motor of a drive unit with motor identification device.
Figure 5:
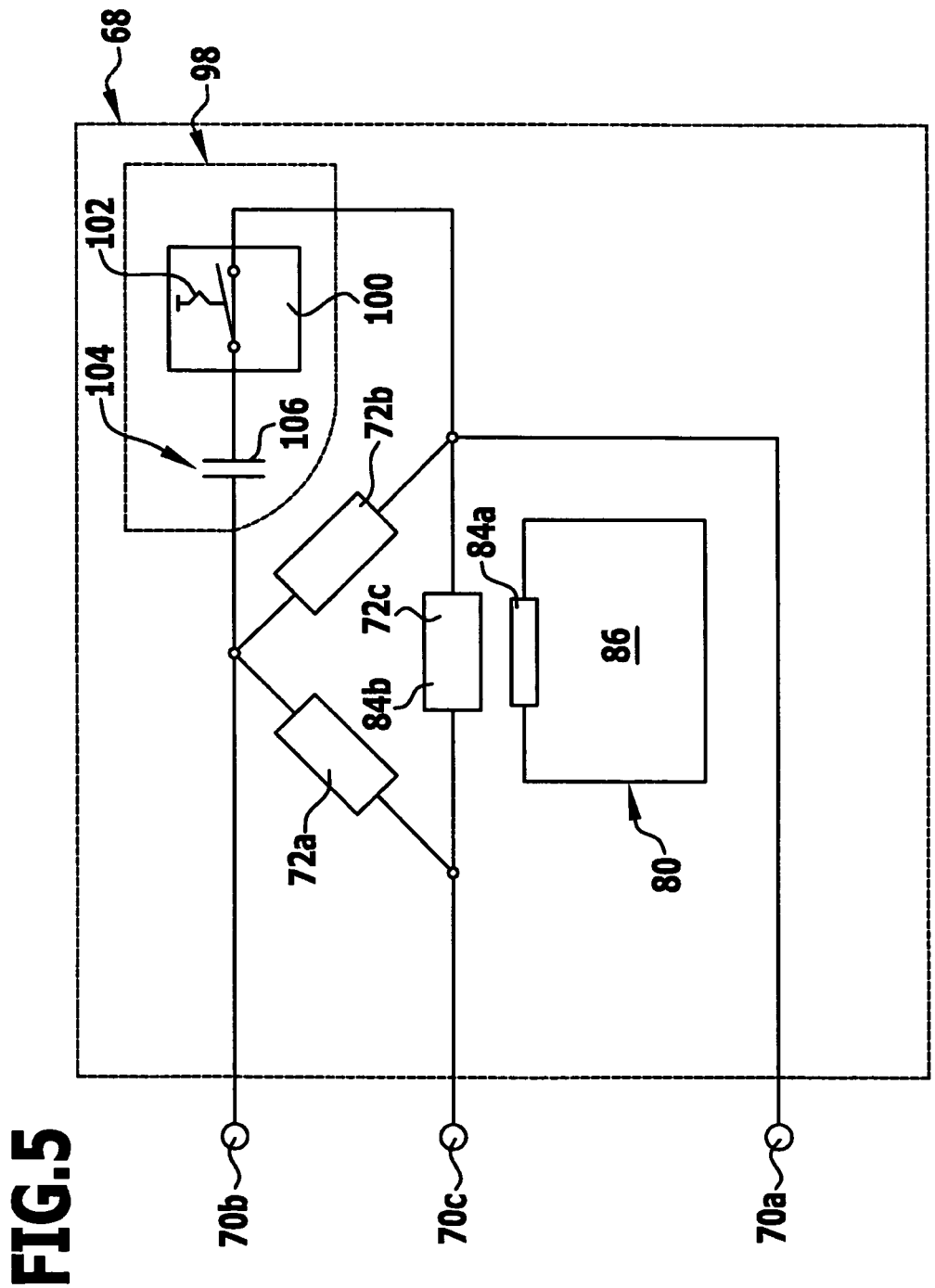
FIG. 5 is a circuit diagram in analogy with FIG. 4 with additional motor disabling device.

FIG. 2 shows diagrammatically the construction of a surgical instrument 60. It comprises a drive unit 14, for example, a drive unit 14a to 14e, and a tool 64, for example, in the form of a drill shown in FIG. 2, connectable to a coupling 62 at the distal end thereof.

There is arranged in a housing 66 of the drive unit 14 a motor 68, which comprises three connection contacts 70a, 70b and 70c, which are each connected to two of a total of three motor windings 72a, 72b and 72c. The connection contact 70a is connected to the motor windings 72b and 72c, the connection contact 70b to the motor windings 72a and 72b, and the connection contact 70c to the motor windings 72a and 72c.

The connection contacts 70a, 70b and 70c are connected by connection lines 74a, 74b and 74c to a coupling element 76 arranged at the proximal end, more particularly, to its connecting contacts 78a, 78b and 78c. For connection to the coupling piece 44 of the connection cable 20, the coupling element 76 is constructed so as to correspond thereto.

The connection cable 20 itself is a three-core connection cable. In the embodiment shown in FIG. 2, no control or data lines are provided at the connection cable 20 or at the drive unit 14.

Furthermore, a motor identification device 80 is integrated into the motor 68. This, in turn, comprises a first transmitting and receiving device 82a in the form of an antenna 84a. The antenna 84a is part of an RFID chip 86, which further comprises an electronic circuit 88, which is connected to the antenna 84a and to a memory device 90 in the form of an electronic data memory. The data memory 92 is preferably a ROM memory, which is non-volatile and non-writable. Stored in the data memory 92 are, in particular, data which characterize the type of motor 68 and/or the type of drive unit 14. Furthermore, the motor identification device 80 may optionally comprise a temperature sensor 94 which is also connected to the circuit 88.

A transmitting and receiving device 82b in the form of an antenna 84b, which is formed by the motor winding 72c, serves for communication with the first transmitting and receiving device 82a. The antenna 84b is, consequently, electrically conductively connected to the connection contacts 70a and 70c.

The transmitting and receiving devices 82a and 82b are arranged in close spatial proximity to each other so that optimum inductive coupling is ensured. Information or data exchange between the transmitting and receiving devices 82a and 82b takes place in a contactless manner by means of electromagnetic waves 96.

The mode of operation of the drive system 10 will be explained briefly hereinbelow. The controller 12 checks in a first inquiry mode, which may also be referred to as standby operation, whether a drive unit 14 is connected to the controller 12. In particular, a check is made as to whether at least one of the motor windings 72a, 72b or 72c is connected to the controller 12 via the connection cable 20. As long as no motor 68, i.e., none of the motor windings 72a, 72b or 72c is recognized, the inquiry is continued.

Once the controller 12 recognizes a motor winding 72a, 72b or 72c contacted with it, then via the motor winding 72c, by correspondingly supplying the connection contacts 70a and 70c with current, the RFID chip 86, which may also be referred to as transponder, is interrogated in a second inquiry mode, i.e., the data stored in the data memory 92 are read out and by communication of the transmitting and receiving devices 82a and 82b read out and transferred to the controller 12. In the controller 12, in accordance with the type of motor detected, stored operational information or parameters can then be read from a memory, not shown, and the controller 12 adjusted accordingly. After detection of the type of motor, in particular, operation of the drive unit 14 can then be started.

Optionally, the drive unit 14 may also be equipped with a motor disabling device 98 which is integrated into the motor 68. It comprises a switch element 100 in the form of a self-retaining button, which has an actuating element 102 projecting at least partially out of the housing 66. Connected in series with the switch element 100 between the connection contacts 70a and 70b is a frequency-dependent resistor 104 in the form of a capacitor 106.

The motor 68 of the drive unit 14 can be disabled as follows: In standby operation (first inquiry mode) of the controller 12, a high-frequency current can also be conducted across the connection contacts 70a and 70b. If the switch element 100 is closed, a high-frequency current between the connection contacts 70a and 70b can flow through the capacitor 106 which is then conductive. If the switch element 100 is open, a current flow is not possible. An intelligent motor disabling function can thus be integrated. The inquiring of the drive unit 14 as to whether the motor disabling device 98 defines a disabling position in which the motor 68 is not to be supplied with current, or an enabling position in which the motor 68 is to be supplied with current, can take place in a third inquiry mode, more particularly, before or after the inquiring as to the type of motor. The detected position of the motor disabling device 98 is taken over in the controller 12, and in dependence upon the detected position, operation of the motor 68 either takes place in accordance with a speed requirement, for example, via the foot control 24, or not. If the speed requirement is reset to zero, the motor 68 is braked to a standstill and the inquiry modes are activated again in the manner described above.

The temperature sensor 94 can be employed, using a software model stored in the controller 12, to calculate the operating temperature reached during operation in the motor 68. The software model is based, in particular, on the assumption that the environmental temperature has a certain value $T_u$, for example, 25° C., and that the motor temperature $T_M$ corresponds to the environmental temperature $T_u$, also 25° C., for example, before the motor is first activated. Owing to the known constructional design of the motor 68, its thermal capacity is known. Furthermore, with the controller 12 the amount of current transported per time unit into the motor 68 during operation is known. With a computer unit, a so-called DSP control, integrated in the controller 12, it is possible to reproduce the motor heating curves and in the rest phases the motor cooling curves. The software model is reset by separating the motor 68 from the motor controller 12.

The accuracy of the motor temperature detection can be improved by the temperature sensor 94. Before the motor 68 is first activated, after each contacting of the motor 68 with the controller 12 and also in the rest phases between two activation cycles the motor temperature is read out using the transmitting and receiving devices 82a and 82b, and the motor temperature calculated by the software model is corrected accordingly. It is thus possible, not only to detect the motor temperature much more precisely than without a temperature sensor, but also, prior to a first activation, to already prevent an unacceptable further activation of a motor 68, which at that point in time is already overheated, by appropriate disabling by means of the controller 12. Optionally, the temperature detecting task could also be assumed by a further RFID chip, which could be integrated into the motor 68 or the drive unit 14.

What is claimed is:

1. Surgical drive system comprising:
at least one control device; and
at least two surgical drive units connectable to and controllable by said at least one control device, or surgical instruments comprising the at least two surgical drive units, at least one of the at least two surgical drive units comprising:
a motor with at least two motor windings,
a memory device for storing data characterizing at least one of the drive unit and the motor;
a first transmitting and receiving device, which is connected to the memory device, and
a second transmitting and receiving device, which is connected to at least two connection contacts of the motor; and wherein:
the first and second transmitting and receiving devices are configured and interact in such a way that data are transferable between them in a contactless manner;
one of the at least two motor windings comprises the second transmitting and receiving device; and
the at least one control device is so configured that when one of the at least two surgical drive units is connected to the at least one control device, it is possible, in one inquiry mode, using the first and second transmitting devices, to read and transfer to the at least one control device the data stored in the memory device.

2. A surgical drive system in accordance with claim 1, wherein at least one of the first and second transmitting and receiving devices is configured as an antenna.

3. A surgical drive system in accordance with claim 1, wherein the data stored in the memory device is transferable in a contactless manner between the first and second transmitting and receiving devices.

4. A surgical drive system in accordance with claim 1, wherein the first and second transmitting and receiving devices are configured for transmitting and receiving electromagnetic waves.

5. A surgical drive system in accordance with claim 1, wherein the first and second transmitting and receiving devices are coupled in a contactless manner to each other.

6. A surgical drive system in accordance with claim 5, wherein the first and second transmitting and receiving devices are inductively coupled to each other.

7. A surgical drive system in accordance with claim 1, further comprising a motor identification device for identifying a kind or type of at least one of the at least two surgical drive units and the motor.

8. A surgical drive system in accordance with claim 7, wherein the motor identification device comprises the first transmitting and receiving device.

9. A surgical drive system in accordance with claim 7, wherein the motor identification device is configured as an RFID (radio-frequency identification) component.

10. A surgical drive system in accordance with claim 7, wherein the motor identification device is arranged in close spatial proximity to the second transmitting and receiving device.

11. A surgical drive system in accordance with claim 1, wherein electromagnetic high-frequency fields of short range are generatable with at least one of the first and second transmitting and receiving devices.

12. A surgical drive system in accordance with claim 1, further comprising a motor disabling device for disabling operation of the motor.

13. A surgical drive system in accordance with claim 12, wherein the motor disabling device comprises:
a switch element which is connected to two motor connection contacts, and
a frequency-dependent resistor connected in series with the switch element between the two motor connection contacts.

14. A surgical drive system in accordance with claim 1, further comprising a temperature sensor.

15. A surgical drive system in accordance with claim 1, further comprising:
a surgical tool connected or connectable to at least one of the at least two surgical drive units and drivable by at least one of the at least two surgical drive units.

16. Surgical instrument in accordance with claim 15, further comprising a motor disabling device for disabling operation of the motor.

17. Surgical drive system in accordance with claim 1, wherein at least one of the at least two surgical drive units further comprises a motor disabling device for disabling operation of the motor.

18. Surgical drive system in accordance with claim 17, wherein:
    the at least two surgical drive units are connected to the control device via connection cables; and
    the connection cables only comprise as many lines as motor windings comprised by the motor.

19. Surgical drive system in accordance with claim 17, wherein:
    the motor disabling device comprises a switch element which is connected to two motor connection contacts; and
    the at least one control device is so configured that when one of the at least two surgical drive units is connected to the at least one control device, it is possible, in a further inquiry mode, by conducting a high-frequency current across the connection contacts connected to the motor disabling device, to detect whether the switch element is open or closed.

20. Surgical drive system in accordance with claim 19, wherein the control device is so configured that the motor is only supplied with current if it has been detected in the further inquiry mode that the switch element is closed.

21. Surgical drive system in accordance with claim 1, wherein the at least one control device is so configured that it is possible, in another inquiry mode, to detect whether one of the at least two surgical drive units is connected to the at least one control device.

22. Surgical drive system in accordance with claim 1, wherein the control device is so configured that temperature data determined with a temperature sensor are readable and transferable to the control device using the first and second transmitting and receiving devices.

23. Surgical drive system in accordance with claim 1, wherein the control device is so configured that operational parameters for operating one of the at least two surgical drive units connected to the control device are automatically set in dependence upon the data read from the memory device.

24. Surgical drive system comprising:
    at least one control device; and
    at least two surgical drive units connectable to and controllable by said at least one control device, or surgical instruments comprising the at least two surgical drive units, at least one of the at least two surgical drive units comprising:
        a motor with at least two motor windings,
        a memory device for storing data characterizing at least one of the drive unit and the motor;
        a first transmitting and receiving device, which is connected to the memory device, and
        a second transmitting and receiving device, which is connected to at least two connection contacts of the motor; and
    wherein:
        the first and second transmitting and receiving devices are configured and interact in such a way that data are transferable between them in a contactless manner;
        one of the at least two motor windings comprises the second transmitting and receiving device; and
        the at least one control device is so configured such that it is possible, in an inquiry mode, to detect whether one of the at least two surgical drive units is connected to the at least one control device.

\* \* \* \* \*